United States Patent
Akimoto et al.

(10) Patent No.: US 10,126,168 B1
(45) Date of Patent: Nov. 13, 2018

(54) OPTICAL SENSOR

(71) Applicant: KABUSHIKI KAISHA TOSHIBA, Minato-ku (JP)

(72) Inventors: Yosuke Akimoto, Yokohama (JP); Shouhei Kousai, Yokohama (JP); Kaita Imai, Tokyo (JP); Michihiko Nishigaki, Kawasaki (JP); Yutaka Onozuka, Yokohama (JP); Miyu Nagai, Kawasaki (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 15/911,349

(22) Filed: Mar. 5, 2018

(30) Foreign Application Priority Data

Aug. 30, 2017 (JP) .................................. 2017-165561

(51) Int. Cl.
- *G01T 1/20* (2006.01)
- *G01J 1/58* (2006.01)
- *G01J 1/04* (2006.01)

(52) U.S. Cl.
CPC ............... *G01J 1/58* (2013.01); *G01J 1/0492* (2013.01)

(58) Field of Classification Search
CPC ......... H01L 27/14623; H01L 27/14627; H01L 31/02165; H01L 31/022416; H01L 27/1464; H01L 31/03046

See application file for complete search history.

(56) References Cited

U.S. PATENT DOCUMENTS

| | | | | |
|---|---|---|---|---|
| 4,941,029 A | * | 7/1990 | Bluzer | H01L 27/14818 257/222 |
| 5,028,970 A | * | 7/1991 | Masatoshi | H01L 27/14831 257/226 |
| 6,112,107 A | * | 8/2000 | Hannula | A61B 5/14552 600/310 |
| 7,095,089 B2 | * | 8/2006 | Yagi | G01J 1/42 257/431 |
| 9,910,161 B1 | * | 3/2018 | Tonami | G01T 1/1603 |
| 2005/0141104 A1 | * | 6/2005 | Hong | H01L 27/14618 359/727 |
| 2010/0201834 A1 | * | 8/2010 | Maruyama | H01L 31/18 348/222.1 |
| 2012/0288920 A1 | | 11/2012 | Takeda | |

(Continued)

FOREIGN PATENT DOCUMENTS

| | | |
|---|---|---|
| JP | 2007-207789 | 8/2007 |
| JP | 4332628 | 9/2009 |
| JP | 2016-099253 | 5/2016 |

(Continued)

*Primary Examiner* — Kiho Kim

(74) *Attorney, Agent, or Firm* — Oblon, McClelland, Maier & Neustadt, L.L.P.

(57) ABSTRACT

According to one embodiment, an optical sensor includes a first substrate, a first insulating film and a light-shielding film. The first substrate has a light detecting region detecting fluorescence generated from a fluorescent material by light with which irradiation is performed from a lateral side. The first insulating film is provided on the first substrate. The light-shielding film is provided, at least, on a side surface of the first substrate to which the light enters, on a side surface of the first insulating film and above a region excluding a region corresponding to the light detecting region of the first insulating film.

20 Claims, 19 Drawing Sheets

(56) References Cited

U.S. PATENT DOCUMENTS

2014/0063303 A1* 3/2014 Masuda ............ H01L 27/14625
348/294
2017/0268982 A1 9/2017 Kousai et al.

FOREIGN PATENT DOCUMENTS

JP 2017-166910 9/2017
WO WO 2011/086990 A1 7/2011

* cited by examiner

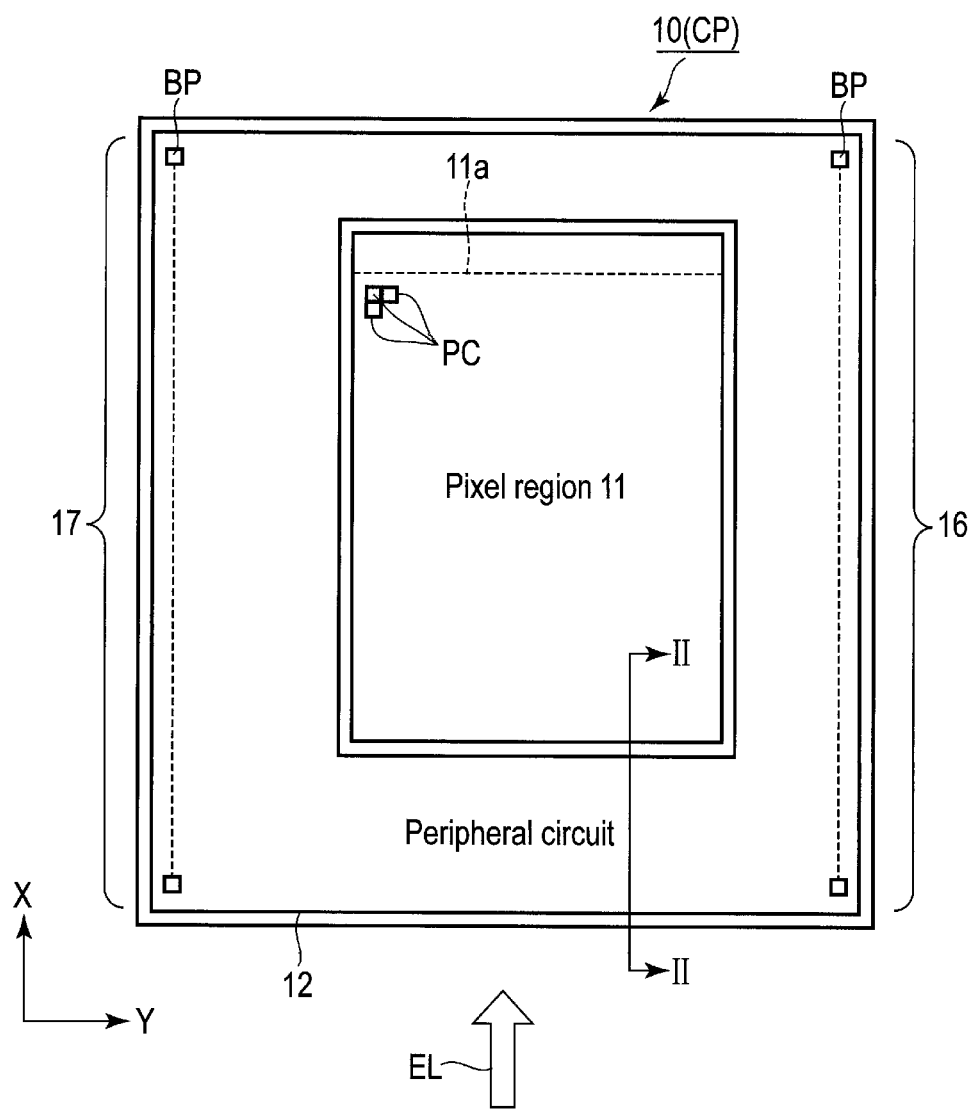
F I G. 1

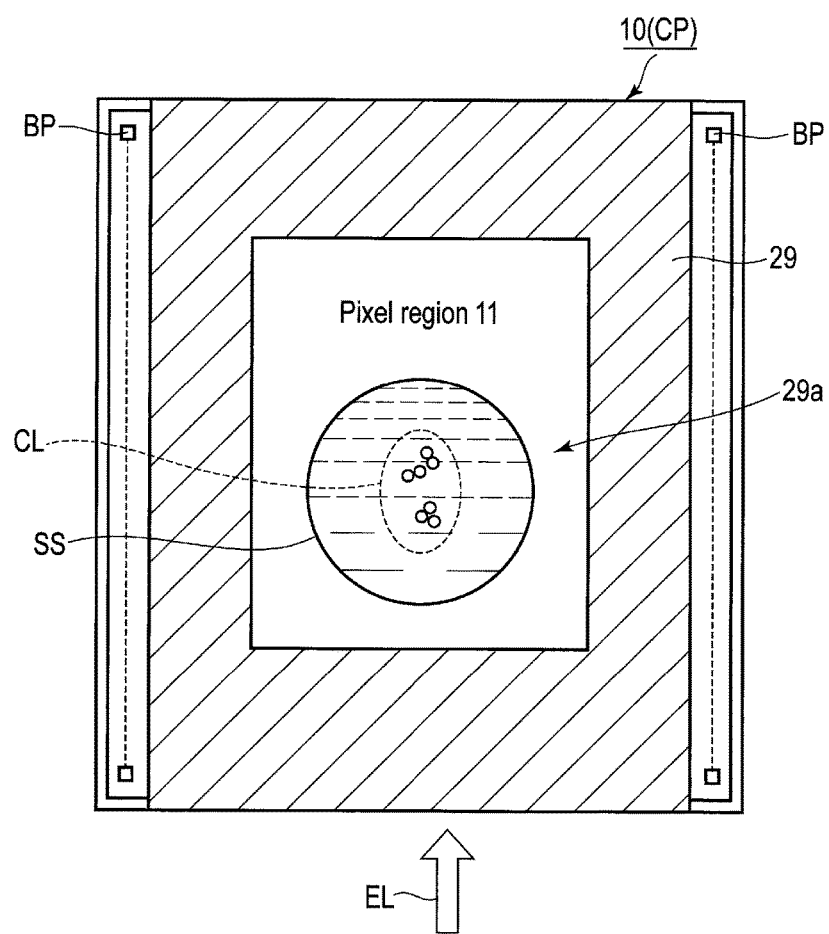
F I G. 3

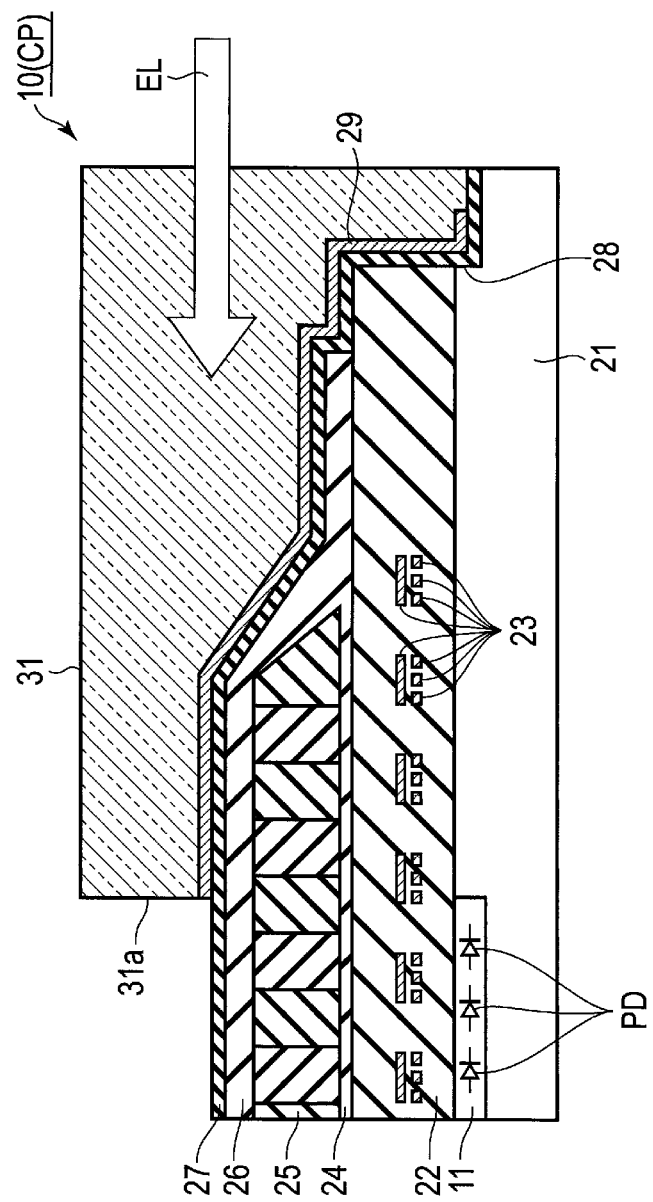
F I G. 9

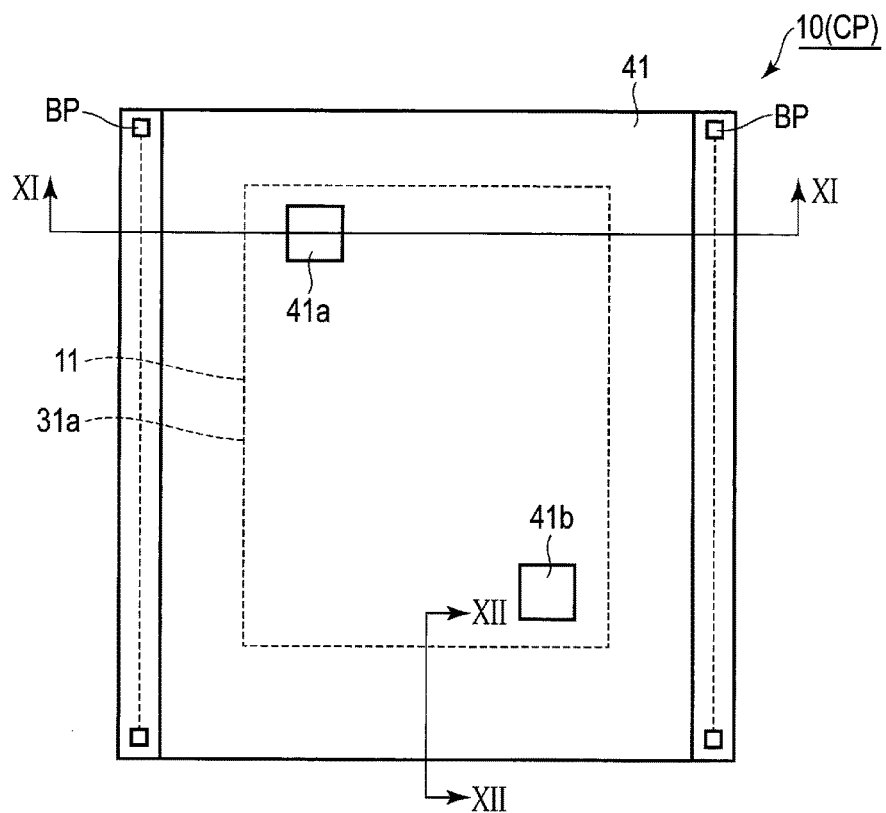
F I G. 10
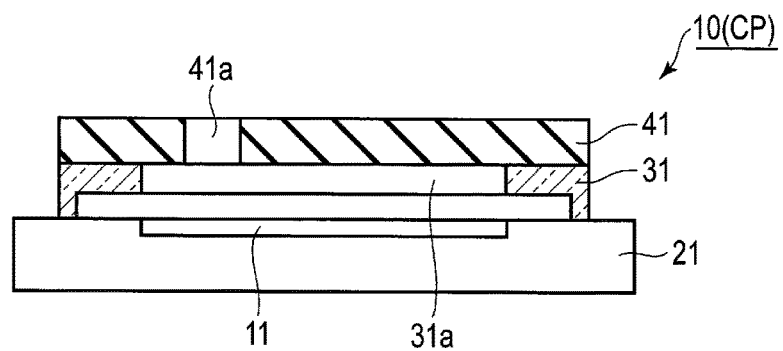
F I G. 11

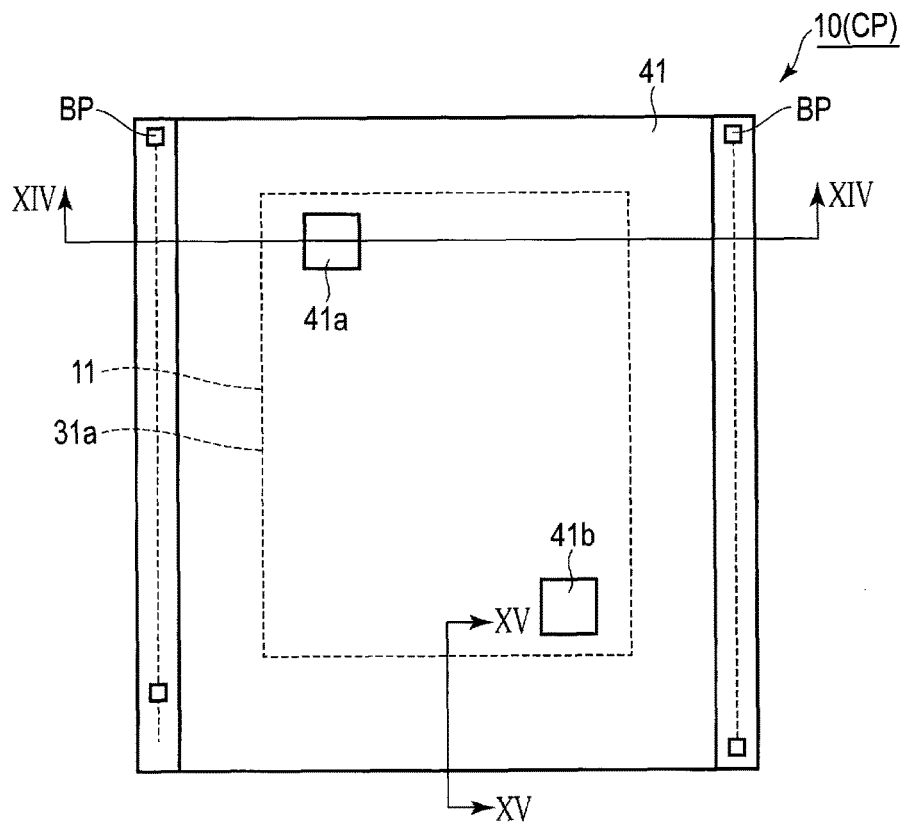
F I G. 13
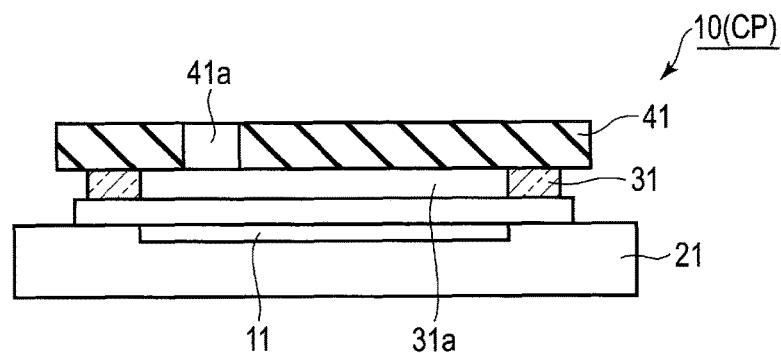
F I G. 14

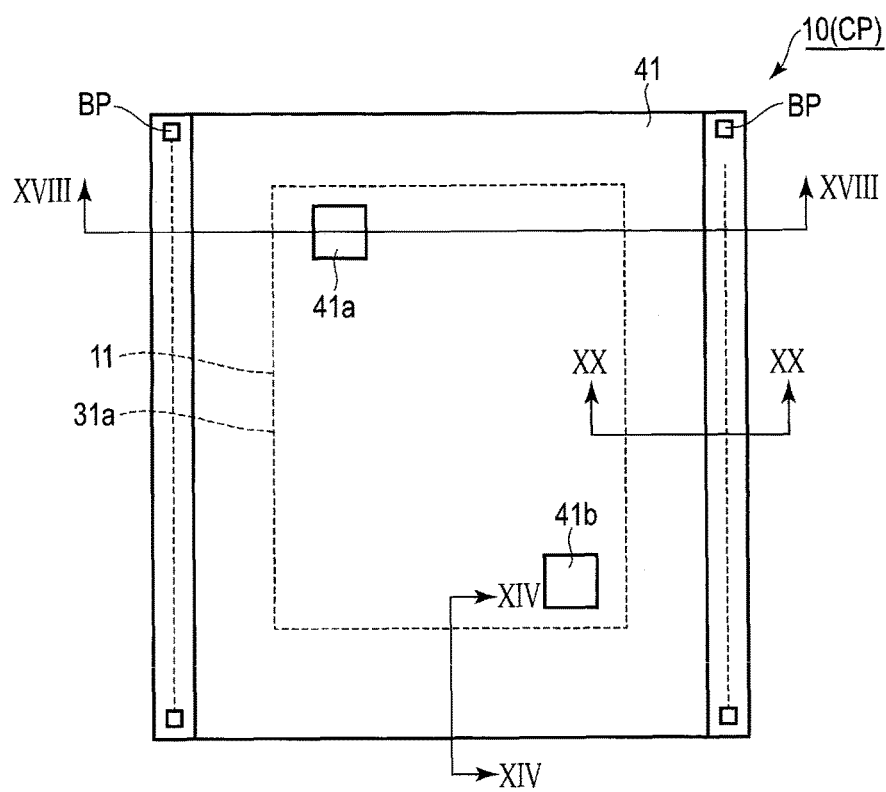
F I G. 17
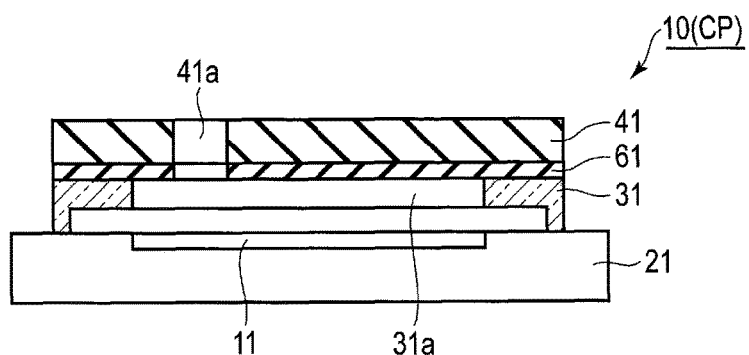
F I G. 18

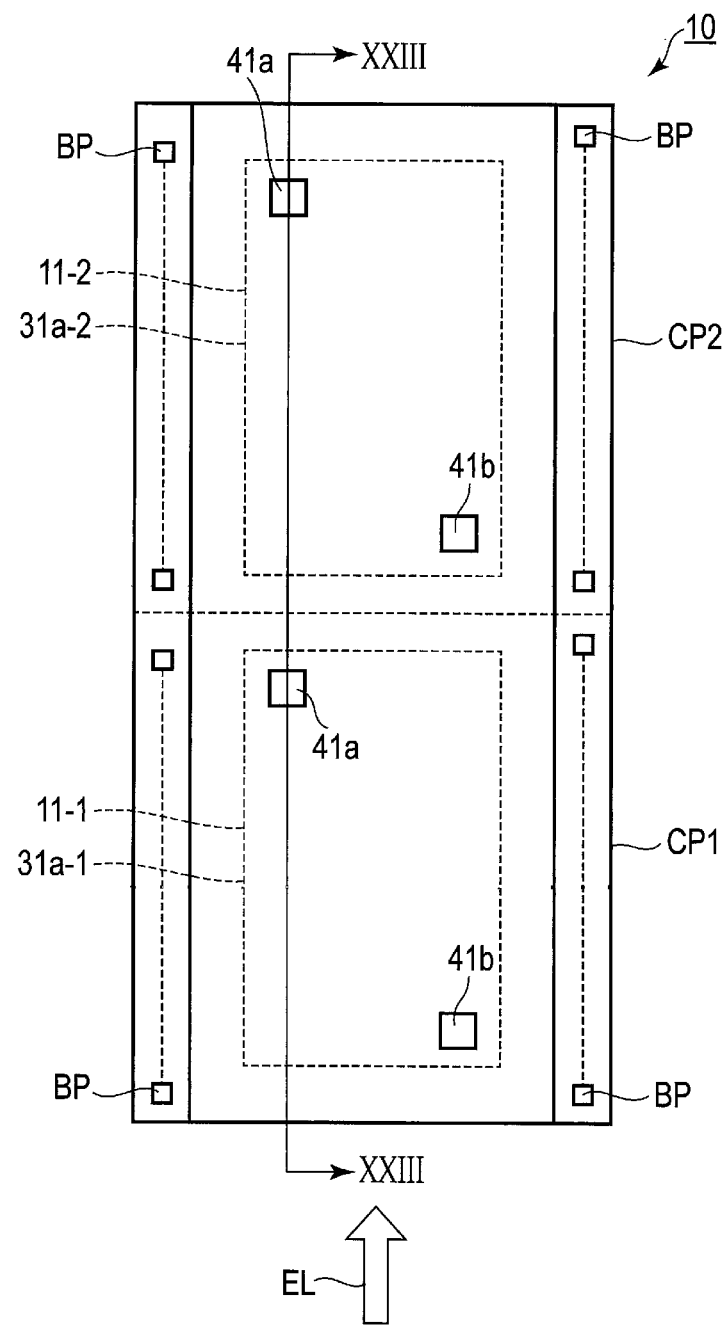
F I G. 22

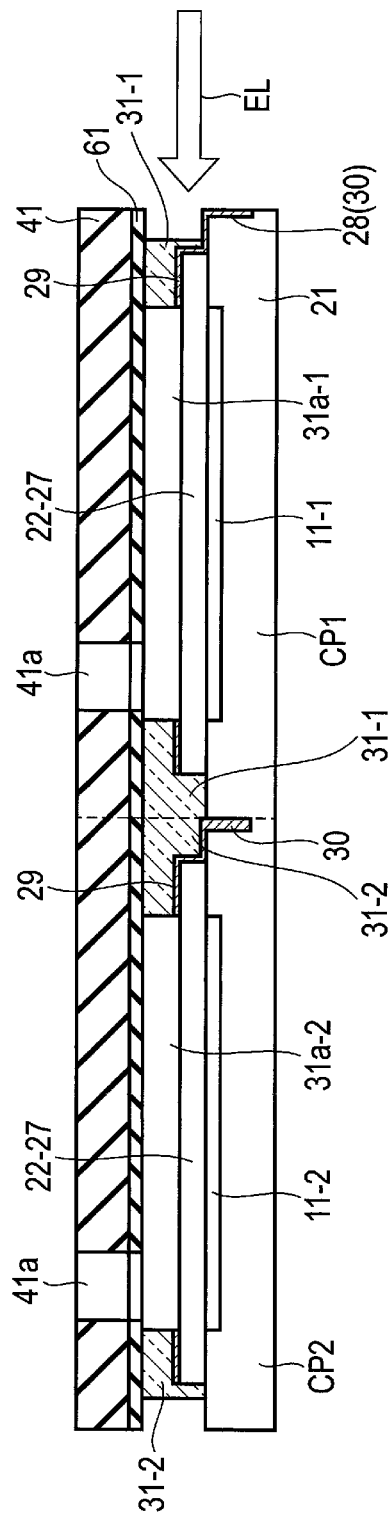
F I G. 23

OPTICAL SENSOR

CROSS-REFERENCE TO RELATED APPLICATIONS

This application is based upon and claims the benefit of priority from Japanese Patent Application No. 2017-165561, filed Aug. 30, 2017, the entire contents of which are incorporated herein by reference.

FIELD

Embodiments described herein relate generally to an optical sensor that detects fluorescence generated from, for example, a cell, as a fluorescent material included in, for example, a specimen solution.

BACKGROUND

In a field such as cell biology, when a specimen solution is irradiated with excitation light such as laser light, fluorescence is generated from a specific fluorescence-stained cell included in the specimen solution. Conventionally, the fluorescence is observed by a fluorescence microscope. However, it has been possible to detect the fluorescence generated from the cell by an optical sensor using a semiconductor.

When the fluorescence generated from the cell in the specimen solution is detected by the optical sensor, if the excitation light directly enters the optical sensor, or if the excitation light is reflected by a wiring in the optical sensor and enters the optical sensor, such light is detected as a noise. Thus, it is difficult to detect the fluorescence from a specimen with high sensitivity, due to the noise.

Accordingly, it is desired to provide an optical sensor capable of preventing a noise from generating, to detect fluorescence from a specimen with high sensitivity.

BRIEF DESCRIPTION OF THE DRAWINGS

FIG. 1 is a plan view schematically showing an optical sensor according to a first embodiment.

FIG. 3 is a plan view showing a light-shielding film according to the first embodiment.

FIG. 9 is a cross-sectional view taken along line IX-IX of FIG. 7.

FIG. 10 is a plan view schematically showing an optical sensor according to a fourth embodiment.

FIG. 11 is a cross-sectional view taken along line XI-XI of FIG. 10.

FIG. 13 is a plan view schematically showing an optical sensor according to a fifth embodiment.

FIG. 14 is a cross-sectional view taken along line XIV-XIV of FIG. 13.

FIG. 17 is a plan view schematically showing an optical sensor according to a sixth embodiment.

FIG. 18 is a cross-sectional view taken along line XVIII-XVIII of FIG. 17.

FIG. 22 is a cross-sectional view schematically showing an optical sensor according to an eighth embodiment.

FIG. 23 is a cross-sectional view taken along line XXIII-XXIII of FIG. 22.

DETAILED DESCRIPTION

Figure 2:
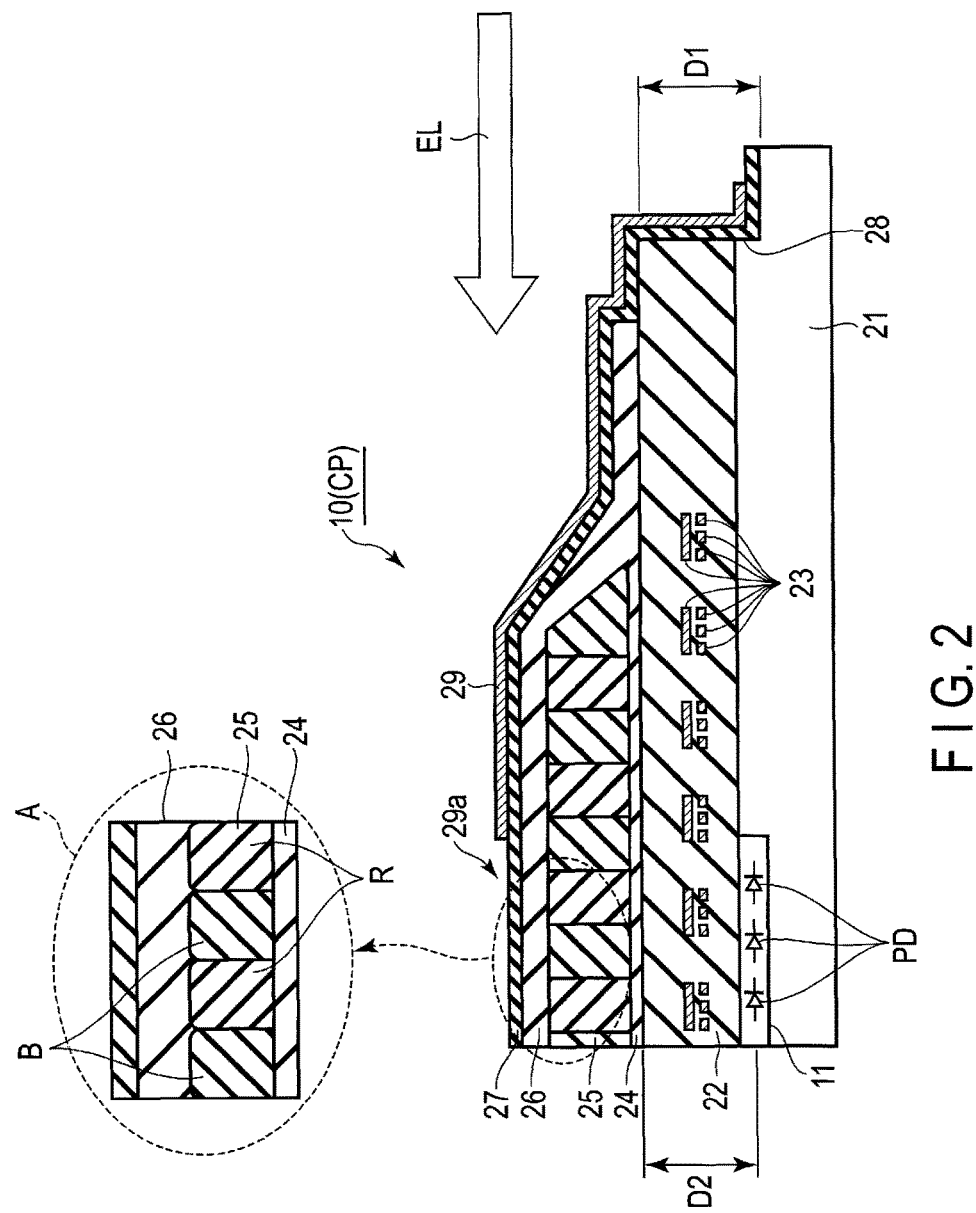
FIG. 2 is a cross-sectional view taken along line II-II of FIG. 1.

In general, according to one embodiment, an optical sensor includes a first substrate, a first insulating film and a light-shielding film. The first substrate has a light detecting region detecting fluorescence generated from a fluorescent material by light with which irradiation is performed from a lateral side. The first insulating film is provided on the first substrate. The light-shielding film is provided, at least, on a side surface of the first substrate to which the light enters, on a side surface of the first insulating film and above a region excluding a region corresponding to the light detecting region of the first insulating film.

Embodiments will be described hereinafter with reference to the accompanying drawings. Note that the same portions are denoted by the same reference numbers in the drawing.

First Embodiment

FIG. 1 schematically shows a chip (CP) of an optical sensor 10 according to the first embodiment. The optical sensor 10 is, for example, a CMOS optical sensor. However, for example, the CCD optical sensor may be applied as the optical sensor 10. In the following description, the optical sensor 10 is the CMOS optical sensor. The optical sensor 10 includes, for example, a pixel region 11 as a light detecting region, a peripheral circuit 12, and a plurality of bonding pad groups 16, 17.

The pixel region 11 is arranged in substantially center portion of the optical sensor 10, and is arranged with, for example, a plurality of pixels PC in a row direction (arrow X direction in the drawing) and a column direction (arrow Y direction in the drawing). Each of the pixels PC includes, for example, a photodiode not shown as a photoelectric conversion element, and a plurality of MOS transistors that select and drive the photodiode. Further, for example, a color filter described later is provided correspondingly to each of the pixels PC. The pixels PC detect fluorescence excited by light from a specific cell included in, for example, specimen solution, through the color filter. A light detection unit is not limited to a diode array including a plurality of photodiodes and may be composed by one photodiode.

The pixel region 11 includes a black pixel region 11a in which light is shielded, and a black level signal is generated.

Configuration of pixels included in the black pixel region 11a is similar to that of the pixels PC included in the pixel region 11.

The peripheral circuit 12 is arranged in, for example, the periphery of the pixel region 11. The peripheral circuit 12 includes: a row selection circuit that selects, for example, the pixels PC arranged in each row; a column parallel A/D conversion circuit that reads a signal from the pixels PC; and a logic circuit that controls the row selection circuit and the column parallel A/D conversion circuit to input and output a signal. Individual functions and arrangement of the peripheral circuit 12 are not limited thereto, and may be varied.

Each of the bonding pad groups 16, 17 includes a plurality of bonding pads BP. The bonding pad group 16 is, for example, arranged along a first side of the peripheral circuit 12. The bonding pad group 17 is, for example, arranged along a second side that is parallel with the first side of the peripheral circuit 12.

The configuration of the pixel region 11 and the peripheral circuit 12, and the arrangement of the bonding pad groups 16, 17 are not limited to those described above, and may be varied.

The optical sensor 10 detects fluorescence excited by excitation light EL from a specified cell as a fluorescent material included in, for example, a specimen solution. For example, laser light is used as the excitation light EL. As the excitation light EL, for example, a semiconductor laser having a wavelength in a range from ultraviolet to visible light may be applied. The wavelength of the laser light is selected depending on a wavelength of fluorescence to be detected.

Irradiation with the excitation light EL is performed from a lateral side of the optical sensor 10 (chip CP), along the bonding pad groups 16, 17. That is, the excitation light EL is irradiated substantially in parallel to a surface of the pixel region 11 from a horizontal direction of the cell included in the specimen solution. Thus, the pixel region 11 can detect the fluorescence from the cell while hardly detecting the excitation light EL.

As for the excitation light EL, it is preferable to irradiate in parallel to the surface of the chip CP (pixel region 11). That is, it is desirable for not detecting the excitation light EL as a noise, that the irradiation with the excitation light EL is performed in parallel to the surface of the pixel region 11.

FIG. 2 shows a cross-section taken along line II-II of FIG. 1.

The optical sensor 10 includes, for example, a substrate 21. For example, a silicon substrate is applied as the substrate 21. The pixel region 11 and the peripheral circuit 12 are provided in the substrate 21. The peripheral circuit 12 is omitted in FIG. 2. The pixel region 11 includes the plurality of photodiodes PD, and the plurality of MOS transistors not shown, that are described above.

An insulating film 22 is provided on the substrate 21. The insulating film 22 is composed of an insulating film having a light-transmitting property, such as a silicon oxide film ($SiO_2$). A plurality of wirings 23 connected to the pixel region 11 and the peripheral circuit 12, and a contact plug not shown are provided in the insulating film 22. The wirings 23 and the contact plug are formed of, for example, a metal material.

An insulating film 24 is provided on the insulating film 22, and, for example, a color filter layer 25 is provided on the insulating film 24. The color filter layer 25 includes, for example, red (R) and blue (B) filters. The red (R) and blue (B) filters are arranged correspondingly to the photodiodes PD. The red (R) and blue (B) filters may be arranged in stripes, and may be arranged in lattice. The color filter layer 25 may include not only the red (R) and blue (B) filters but also a green (G) filter. The color filter layer 25 may include a single color of red, blue, green, or the like.

The insulating film 24 is a light-transmitting insulating film. For example, an acrylic resin material may be applied as the insulating film 24. Providing the insulating film 24 can improve adhesion between the insulating film 22 and the color filter layer 25. When the insulating film 22 and the color filter layer 25 can be adhered to each other, the insulating film 24 can be omitted.

An insulating film 26 as a protective film is provided on the color filter layer 25 and the insulating film 24. The insulating film 26 is provided so as to cover an upper surface and a side surface of the color filter layer 25. As similar to the insulating film 24, for example, an acrylic resin material may be applied as the insulating film 26.

The surface of the color filter layer 25 is not flat as shown in a part in FIG. 2. For example, by spin-coating the upper surface of the color filter 25 with an acrylic resin material as the insulating film 26, the insulating film 26 having a flat surface can be provided on the color filter layer 25. Thereby, the insulating film 26 can prevent light from scattering.

In the substrate 21 and the insulating film 22, for example, in a state of wafer, a stepped portion 28 is formed by reactive ion etching (RIE) or half cutting such as dicing, to expose side surfaces of the substrate 21 and the insulating film 22. The portion formed with the stepped portion 28 is, for example, a side of the chip CP irradiated with the excitation light EL.

A depth (a distance from an upper surface of the insulating film 22 to a bottom portion of the substrate 21) D1 of the stepped portion 28 is made deeper than a depth (a distance from the upper surface of the insulating film 22 to the photodiodes PD in the substrate 21) D2 in which the photodiodes PD in the pixel region 11 are formed.

A light-transmitting insulating film, for example, an inorganic insulating film 27 is provided on the entire surface of the insulating film 26 and the insulating film 22, and a side surface and a bottom surface of the stepped portion 28. For example, a silicon oxide film, a silicon nitride film (SiN), a silicon oxynitride film (SiON), or the like can be applied as the insulating film 27. It is preferable that the insulating film 27 is formed by using, for example, chemical vapor deposition (CVD) by which a film can be deposited in low temperature of 200° C. or lower.

As shown in FIG. 2 and FIG. 3, a light-shielding film 29 is provided on the insulating film 27, and at least on a side surface of the stepped portion 28, excluding the pixel region 11 and the region where the bonding pad BP is formed. That is, the light-shielding film 29 has an opening 29a corresponding to the pixel region 11, and covers an upper surface of the chip CP excluding the pixel region 11 and the region where the bonding pad BP is formed, and a side surface of the chip CP irradiated with the excitation light EL.

For example, a metal material such as an aluminum (Al) and a titanium (Ti), or an organic material capable of absorbing light of the entire region of visible light, for example, a black filter material can be applied as the light-shielding film 29. When the light-shielding film 29 is formed of a metal material, the insulating film 27 insulates the light-shielding film 29 and the substrate 21.

When the light-shielding film 29 can shield irradiation with the excitation light EL from the lateral side of the chip CP, the noise can be prevented from generating from the wirings 23, and the like. Thus, the light-shielding film 29 only needs to be provided at least in the side surface of the chip CP, and is not necessarily formed on the upper surface of the chip CP.

In the configuration described above, as shown in FIG. 3, when, for example, a specimen solution SS containing a cell CL is dropped into the opening 29a of the light-shielding film 29, and the specimen solution SS is irradiated with the excitation light EL from the lateral side, the specific cell CL in the specimen solution SS is excited by the excitation light EL to generate fluorescence. This fluorescence is detected by the pixels PC that are in the pixel region 11, via the color filter layer 25.

The specimen solution SS may be dropped to part of the pixel region 11. Otherwise, as described later, a light-transmitting thick film material may be provided in the periphery of the pixel region 11, and an accommodation unit that is similar to a petri dish (Schale) may be provided above the pixel region 11 by the thick film material, and the specimen solution SS may be dropped to the entire surface of the pixel region 11 in the accommodation unit. A flow path may be formed above the pixel region 11, and the specimen solution may be flowed through the flow path.

Effect of First Embodiment

According to the first embodiment, the light-shielding film 29 is provided on the insulating film 27 excluding the pixel region 11, and the side surface of the stepped portion 28, and irradiation with the excitation light EL is performed from the side surface side in which the stepped portion 28 of the chip CP is provided, substantially in parallel to the pixel region 11. Thus, irradiation of the excitation light EL performed from the lateral side of the chip CP can be prevented from entering the chip CP, and the pixel region 11 can detect the fluorescence generated from the cell in high sensitivity.

The light-shielding film 29 is formed in the side surface of the stepped portion 28, and the depth D1 of the stepped portion 28 is deeper than the depth D2 in which the photodiodes PD of the pixel region 11 are formed. Thus, since the light-shielding film 29 can shield the light advancing from the lateral side of the substrate 21 and the insulating film 22 toward the photodiodes PD, scattered light as the noise can be prevented from generating from the plurality of wirings 23 in the insulating film 22.

Figure 4A:
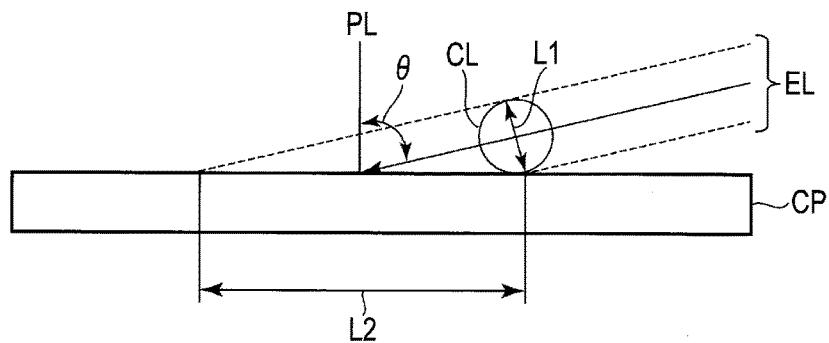
FIG. 4A is a diagram showing a relationship between a cell as a specimen and an incident angle of excitation light.

FIG. 4A shows a relationship between the cell CL as a specimen, and an incident angle θ of the excitation light EL.

As shown in FIG. 4A, when the cell CL as a sphere having a diameter L1 is assumed, and the cell CL on the chip CP is irradiated with the incident angle θ, a shadow of the cell CL having a length L2 is formed on the surface of the chip CP. The incident angle θ is an irradiation angle of the excitation light EL with respect to a perpendicular line PL to the surface of the chip CP. In this case, the removal ratio of the excitation light EL by the cell CL is obtained by 1/L1/L2=1/sin(90−θ).

Figure 4B:
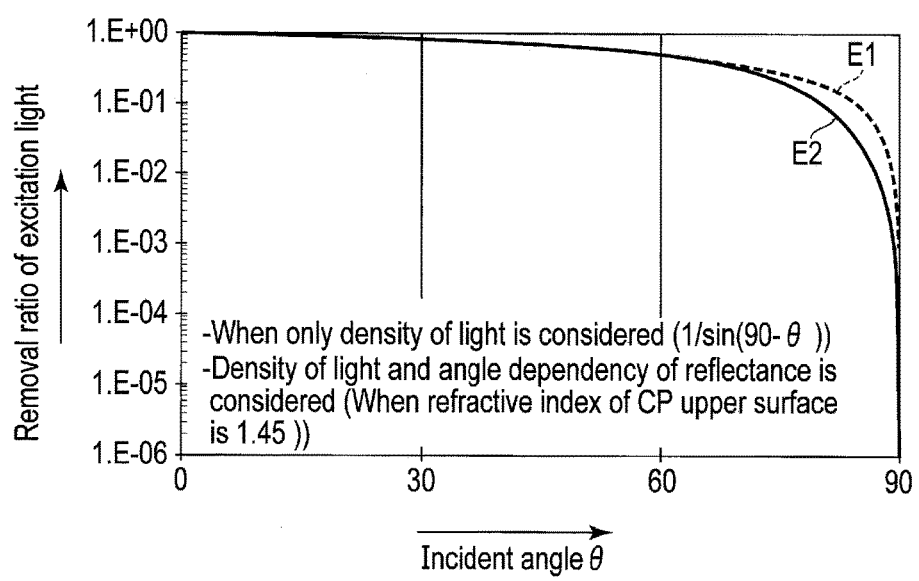
FIG. 4B is a diagram showing a relationship between an incident angle of excitation light EL and a removal ratio of the excitation light.

FIG. 4B is a diagram showing a relationship between the incident angle θ of the excitation light EL and the removal ratio of the excitation light EL by the cell CL.

In FIG. 4B, a characteristic E1 is a characteristic in consideration only the density of the excitation light EL, and a characteristic E2 is a characteristic in consideration with the density of the excitation light EL and angle dependency of the reflectance of the cell CL and the surface of the chip CP (when an refractive index of the upper surface of the chip CP is 1.45).

As is clear from the characteristic E1 and the characteristic E2, the removal ratio of the excitation light EL increases as the incident angle θ with respect to the line PL increases. In other words, the removal ratio of the excitation light EL increases as the incident angle becomes closer to the parallel to the surface of the chip CP. Thus, it is preferable that the incident angle θ of the excitation light EL is, for example, up to about 5°.

More preferably, under a condition in which the cell CL in the specimen solution can be irradiated enough with the excitation light EL from the lateral side, the incident angle θ may be 90° (0° with respect to the surface of the chip CP). In this case, since the removal ratio can be improved to about one millionth, the excitation light EL as the noise can be further preferably removed.

The incident angle θ of 90° or more (minus angle of 0° or less with respect to the surface of the chip CP) is not preferable, since it is difficult to irradiate the cell CL on the chip CP with the excitation light EL.

Figure 5:
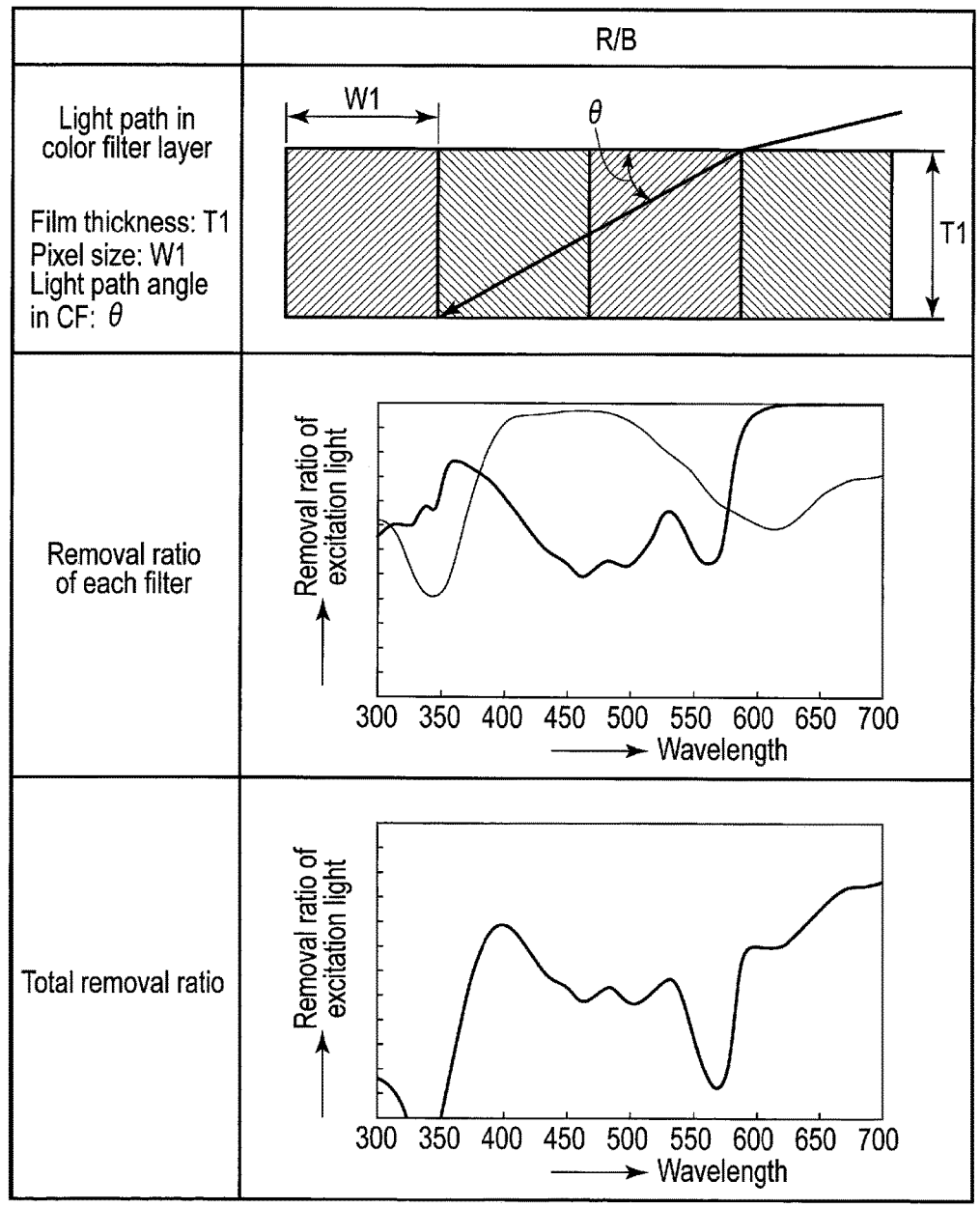
FIG. 5 is a diagram showing a relationship between an absorption wavelength of a color filter and the removal ratio of the excitation light.

FIG. 5 shows a removal ratio of the excitation light EL with respect to an absorption wavelength of the color filter (CF) layer 25.

When a film thickness of the color filter layer 25 is T1, a pixel size is W1, and an angle θ of a light path in the color filter layer 25 is, for example, 30', the light passes the red (R) and blue (B) filter layers, and thereby, the light in the visible light region can be removed. The angle θ of the light path in the color filter layer 25 being, for example, 30° corresponds to a case where the excitation light EL enters the surface of the chip CP with the incident angle of, for example, 1° to 5°. From the relationship between the film thickness T1 and the pixel size W1, the excitation light EL that enters with the incident angle of 1° to 5° passes the plurality of color filters as shown in FIG. 5. Thus, the excitation light EL can be cut irrespective of the wavelength of the excitation light EL. Accordingly, when the excitation light EL enters the surface of the chip CP with the incident angle of, for example, 1° to 5°, the light in the visible light region can be removed, and the fluorescence generated from the cell CL can be detected in high sensitivity.

Second Embodiment

Figure 6:
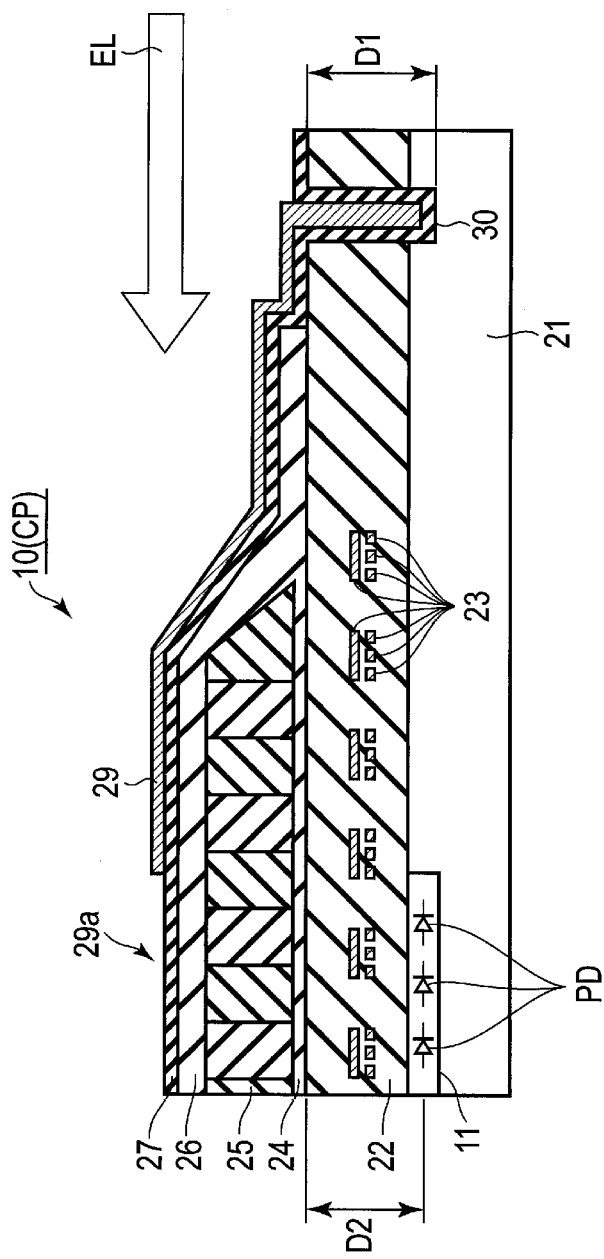
FIG. 6 is a cross-sectional view schematically showing an optical sensor according to a second embodiment.

FIG. 6 shows an optical sensor 10 according to a second embodiment. In the first embodiment, part of a light-shielding film 29 is provided on a stepped portion 28 formed in the chip CP. That is, part of the light-shielding film 29 is provided on the side surface of the chip CP exposed by half cutting by dicing, or etching. Part of the light-shielding film 29 may be formed in the inside of the chip CP.

As shown in FIG. 6, in the second embodiment, part of the light-shielding film 29 is formed in the inside of the chip CP. That is, the chip CP has a groove (recess) 30 at least in the side irradiated with the excitation light EL. The groove 30 is formed by etching an insulating film 22 and the substrate 21 by, for example, RIE, and an insulating film 27 and the light-shielding film 29 are formed in the groove 30. The groove 30 has a depth D1 that is deeper than a depth D2 in which the photodiodes PD in a pixel region 11 are formed as similar to the stepped portion 28.

That is, the substrate 21 comprises the recess (groove 30) in which the light-shielding film 29 is formed, and the depth of the recess is deeper than the position of the layer in which the photodiodes PD is formed.

The groove 30 may be formed not only in the side of the chip CP irradiated with the excitation light EL, but also in the outside of a bonding pad BP when the groove 30 does not affect wirings 23 and the bonding pad BP.

The groove 30, the insulating film 27, and the light-shielding film 29 may be formed in a process of forming the wirings 23, and may be formed in a process after a color filter layer 25 is formed.

Effect of Second Embodiment

As described above, forming part of the shielding film 29 in the inside of the chip CP also can prevent the excitation light EL with which the irradiation is performed from the lateral side of the chip CP, and the scattered light as the noise generated from the wirings 23, or the like, is prevented from being detected by the pixel region 11, as similar to the first embodiment. Accordingly, the fluorescence generated from the cell included in the specimen solution and excited by the excitation light EL can be detected in high sensitivity.

Third Embodiment

Figure 7:
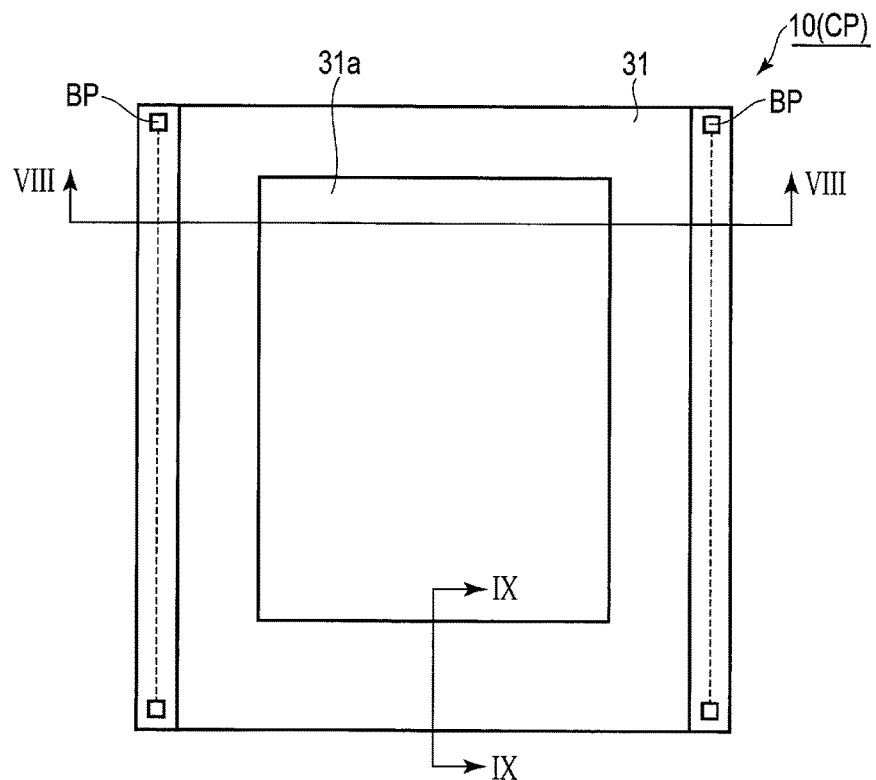
FIG. 7 is a plan view showing a third embodiment.
Figure 8:
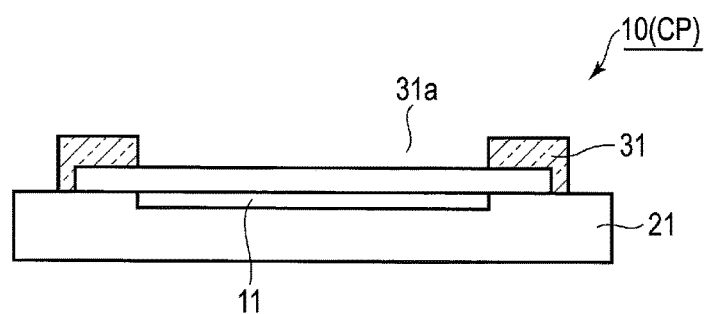
FIG. 8 is a cross-sectional view taken along line VIII-VIII of FIG. 7.

FIGS. 7, 8, and 9 show an optical sensor 10 according to a third embodiment.

In the third embodiment, as shown in FIG. 9, for example, a thick film material 31 having a light-transmitting property on a light-shielding film 29 of a chip CP shown in the first embodiment, and an accommodation unit 31a is provided above a pixel region 11 by the thick film material 31. That is, as shown in FIG. 7, the thick film material 31 is formed on the light-shielding film 29 excluding the region corresponding to the pixel region 11 and the region in which the bonding pad BP is formed. Thus, the thick film material 31 has the accommodation unit 31a that is similar to a petri dish, and corresponds to the pixel region 11, for accommodating the specimen solution.

The thick film material 31 is formed of, for example, polydimethylsiloxane (PDMS). However, the thick film material 31 is not limited thereto. For example, a material having a light-transmitting property, and small light scattering, not generating fluorescence, and having no toxicity to the cell in the specimen solution, may be applied as the thick film material 31.

When the PDMS is used, after the PDMS is applied to a front surface of a wafer by, for example, spin-coating, the PDMS is removed from the region corresponding to the pixel region 11 and the region in which the bonding pad BP is formed by using the RIE, or the like. Otherwise, the PDMS may be formed in a region excluding the region corresponding to the pixel region 11 and the region in which the bonding pad BP is formed, by using the lithographic technique.

In the configuration described above, in a state where the specimen solution is accommodated in the accommodation unit 31a, when the excitation light EL is irradiated from the lateral side of the chip CP, the specific cell in the specimen solution is excited by the excitation light EL that has transmitted through the thick film material 31, and the fluorescence generated from the cell is detected by the photodiodes PD in the pixel region 11 through the color filter layer 25.

In the third embodiment, the accommodation unit 31a is provided on the configuration according to the first embodiment by the thick film material 31. However, the third embodiment is not limited thereto. The accommodation unit 31a may be provided on the configuration according to the second embodiment by the thick film material 31. Also in the embodiments described below, although the configuration according to the first embodiment is varied, the configuration according to the second embodiment may be varied.

Effect of Third Embodiment

According to the third embodiment described above, the accommodation unit 31a corresponding to the pixel region 11 is provided on the light-shielding film 29 by the thick film material 31 having the light-transmitting property. Thus, in a state where the specimen solution is accommodated in the accommodation unit 31a, irradiation with the excitation light EL can be performed from the lateral side of the chip CP. Further, since the thick film material 31 has small light scattering and generates no fluorescence, the fluorescence emitted from the cell in the specimen solution can be detected in high sensitivity.

Fourth Embodiment

Figure 12:
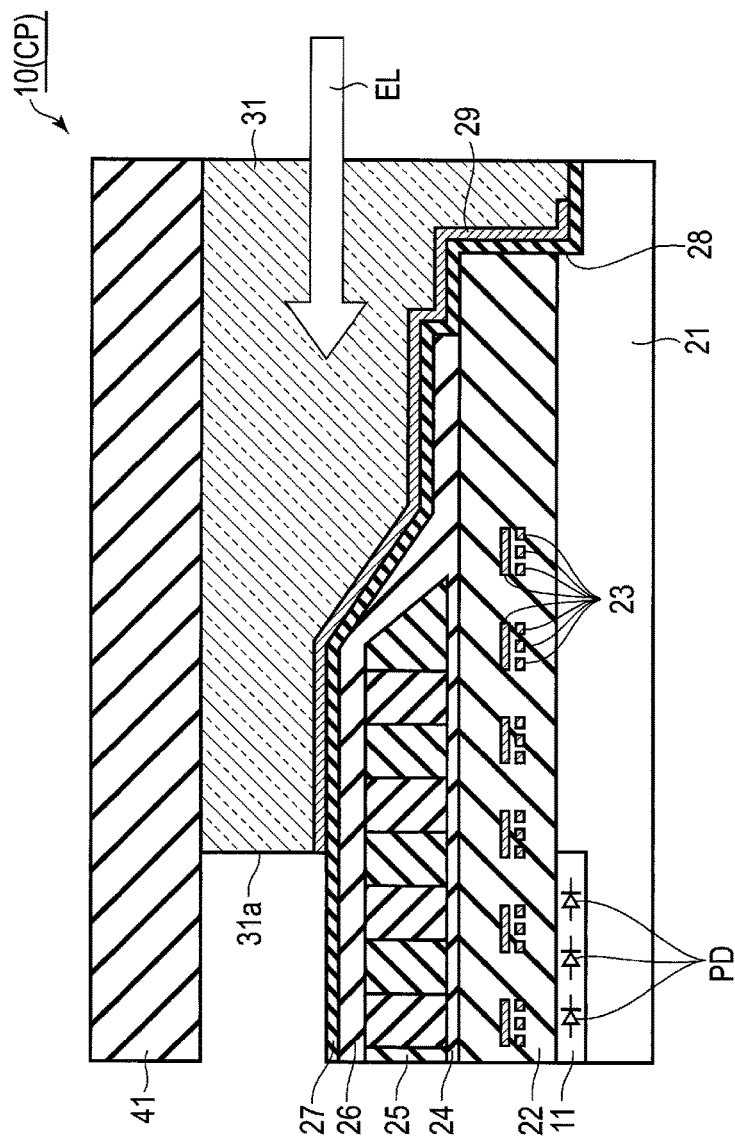
FIG. 12 is a cross-sectional view taken along line XII-XII of FIG. 10.

FIGS. 10, 11, and 12 show an optical sensor 10 according to a fourth embodiment.

The fourth embodiment includes a substrate (hereinafter, referred to as a light shielding substrate) 41 having a light shielding property, in addition to the configuration according to the third embodiment. A light shielding substrate 41 is, for example, a silicon substrate, is provided on a thick film material 31, and covers an accommodation unit 31a. The light shielding substrate 41 is, for example, surface activation bonded to the thick film material 31. Thus, before the bonding, the surface of the light shielding substrate 41 and the surface of the thick film material 31 are processed by, for example, oxygen plasma, and are activated. The bonding means for the light shielding substrate 41 and the thick film material 31 is not limited thereto, and the bonding may be performed by other means.

Since the accommodation unit 31a is covered by the light shielding substrate 41, stray light as unintended light that enters from above the accommodation unit 31a is shielded by the light shielding substrate 41.

The thick film material 31 provided between the light shielding substrate 41 and a light-shielding film 29 functions as a light path. Thus, as shown in FIG. 12, the excitation light EL with which irradiation is performed from the lateral side of the chip CP passes the thick film material 31 as the light path, and the specimen solution in the accommodation unit 31a is irradiated with an excitation light EL. Since the accommodation unit 31a is covered by the light shielding substrate 41, the stray light is blocked. Accordingly, photodiodes PD of a pixel region 11 can detect the fluorescence generated from the cell excited by the excitation light EL in high sensitivity.

As shown in FIG. 10, the light shielding substrate 41 may have openings 41a, 41b, in part of the light shielding substrate 41. Thereby, the specimen solution can be flowed from the opening 41a into the accommodation unit 31a, the specimen solution in the accommodation unit 31a can be discharged from the opening 41b, and the accommodation unit 31a can be used as a flow path.

The number of the openings 41a, 41b is not limited to two, and may be changed according to the purpose of use. The number of the openings may be one, or three or more.

The light shielding substrate 41 is provided on a region excluding the region where the bonding pad BP is arranged. Thus, since the bonding pad BP is not covered by the light shielding substrate 41 and is exposed, wire bonding can be performed.

Effect of Fourth Embodiment

According to the fourth embodiment described above, the accommodation unit 31a is covered by the light shielding substrate 41, entering of the stray light to the accommodation unit 31a is blocked. Accordingly, the photodiodes PD of the pixel region 11 can detect the fluorescence generated from the specific cell in high sensitivity, without detecting the stray light as the noise.

Fifth Embodiment

FIGS. 13, 14, 15, and 16 show an optical sensor 10 according to a fifth embodiment.

The fifth embodiment is a variation of the fourth embodiment. In the fourth embodiment, the light shielding substrate 41 is bonded on the thick film material 31 provided on the light-shielding film 29. That is, the light shielding substrate 41 is provided on the thick film material 31 after the thick film material 31 is formed on the light-shielding film 29.

On the other hand, the fifth embodiment has different configuration and manufacturing process from those of the fourth embodiment.

Figure 15:
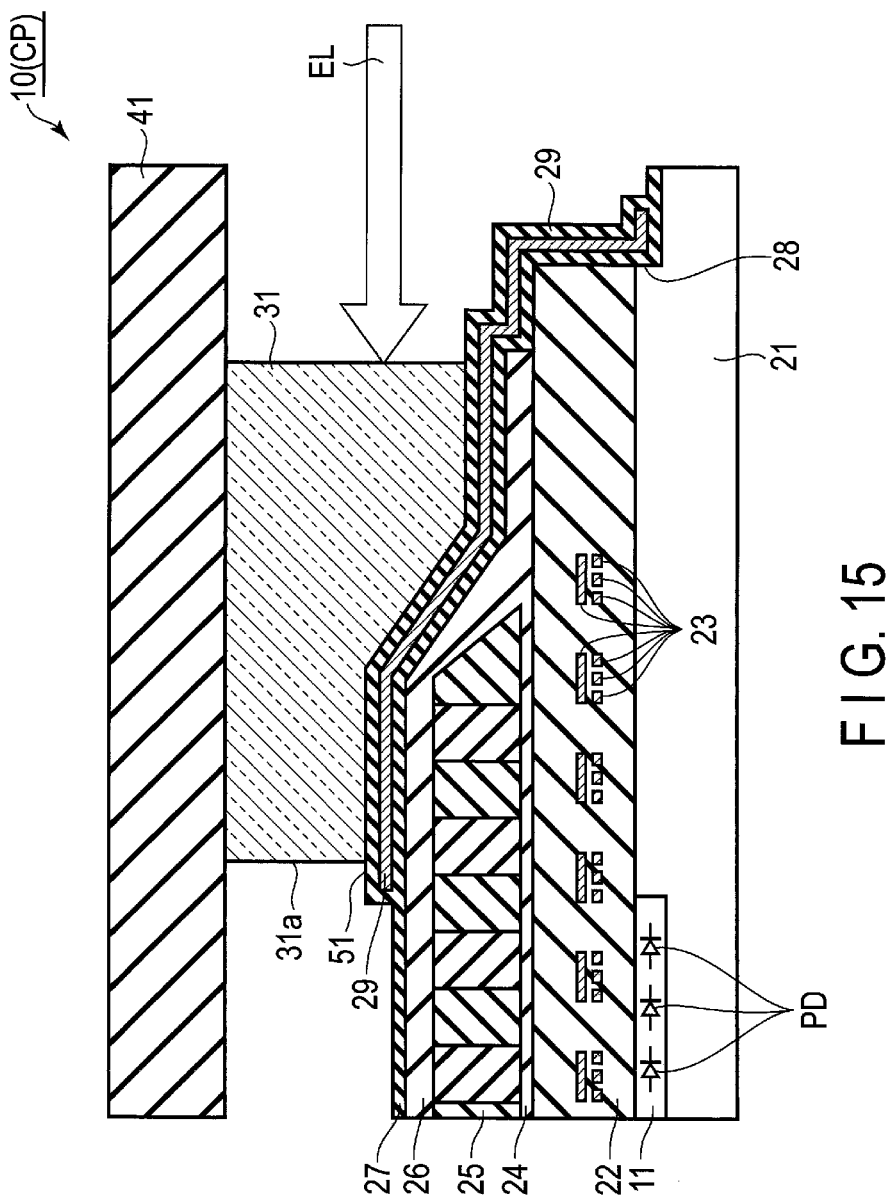
FIG. 15 is a cross-sectional view taken along line XV-XV of FIG. 13.

As shown in FIG. 15, in the fifth embodiment, for example, a silicon oxide film ($SiO_2$) 51 as an insulating film is formed on a light-shielding film 29, and a light shielding substrate 41 formed with a thick film material 31 is bonded on the silicon oxide film 51.

Figure 16:
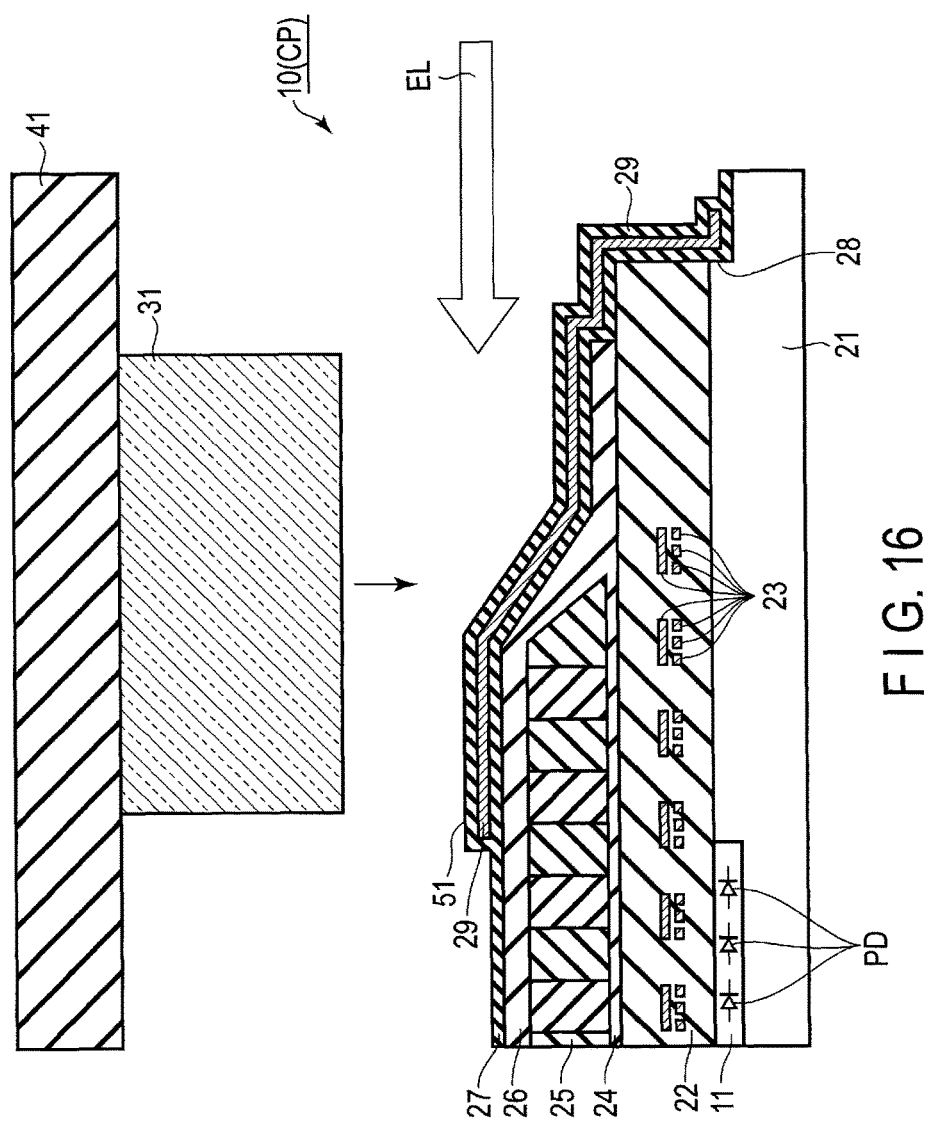
FIG. 16 is a cross-sectional view showing a manufacturing process of FIG. 15.

Specifically, as shown in FIG. 16, the silicon oxide film 51 is formed on the light-shielding film 29, and the surface of the silicon oxide film 51 is processed with, for example, oxygen plasma, and is activated.

On the other hand, the thick film material 31 is formed on the light shielding substrate 41 by another manufacturing process. That is, the thick film material 31 is patterned on the light shielding substrate 41 by, for example, the lithographic technique. Then, the surface of the thick film material 31 is processed by, for example, oxygen plasma, and is activated.

After that, the light shielding substrate 41 formed with the thick film material 31 is bonded to a chip CP so that the thick film material 31 contacts with the silicon oxide film 51. In this state, the thick film material 31 and the silicon oxide film 51 are surface activation bonded, and are formed as shown in FIG. 15.

Effect of Fifth Embodiment

The fifth embodiment can provide a similar effect to that of the fourth embodiment.

Further, according to the fifth embodiment, the light shielding substrate 41 formed with the thick film material 31 only needs to be bonded to the chip CP so as to contact with the silicon oxide film 51. Thus, manufacturing is easy.

Sixth Embodiment

FIGS. 17, 18, 19, and 20 show an optical sensor 10 according to a sixth embodiment.

The sixth embodiment is a variation of the fifth embodiment.

Figure 19:
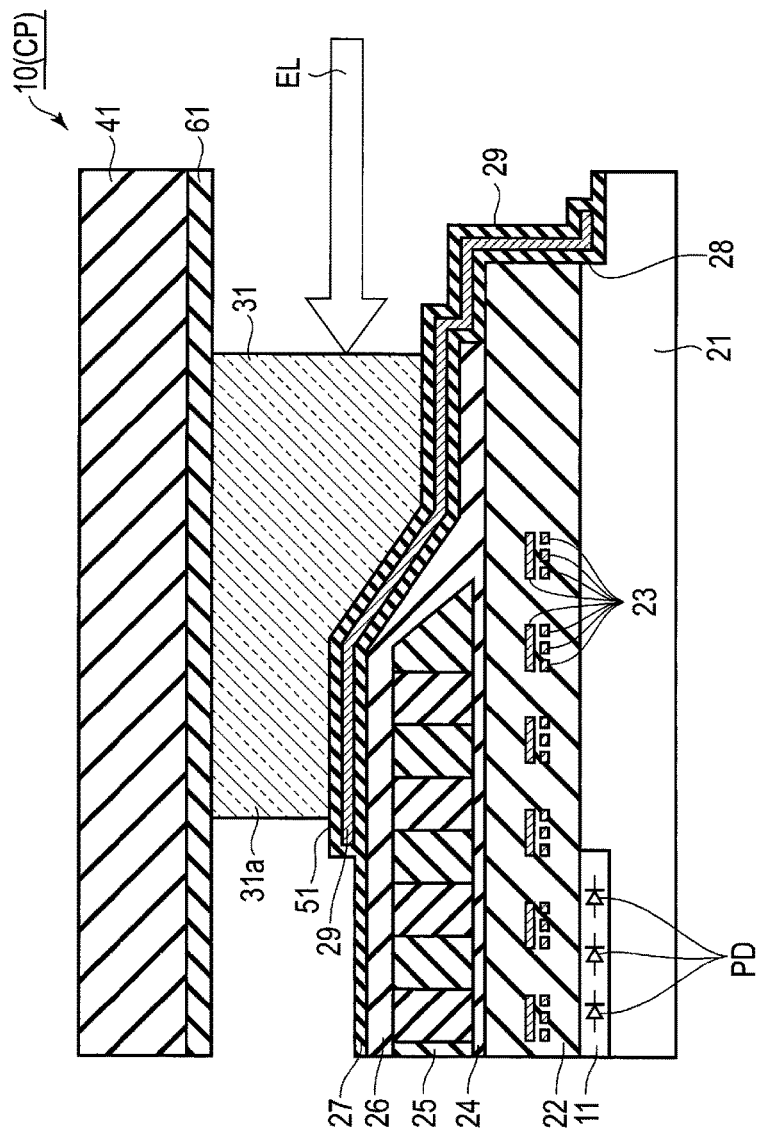
FIG. 19 is a cross-sectional view taken along line XIV-XIV of FIG. 17.
Figure 20:
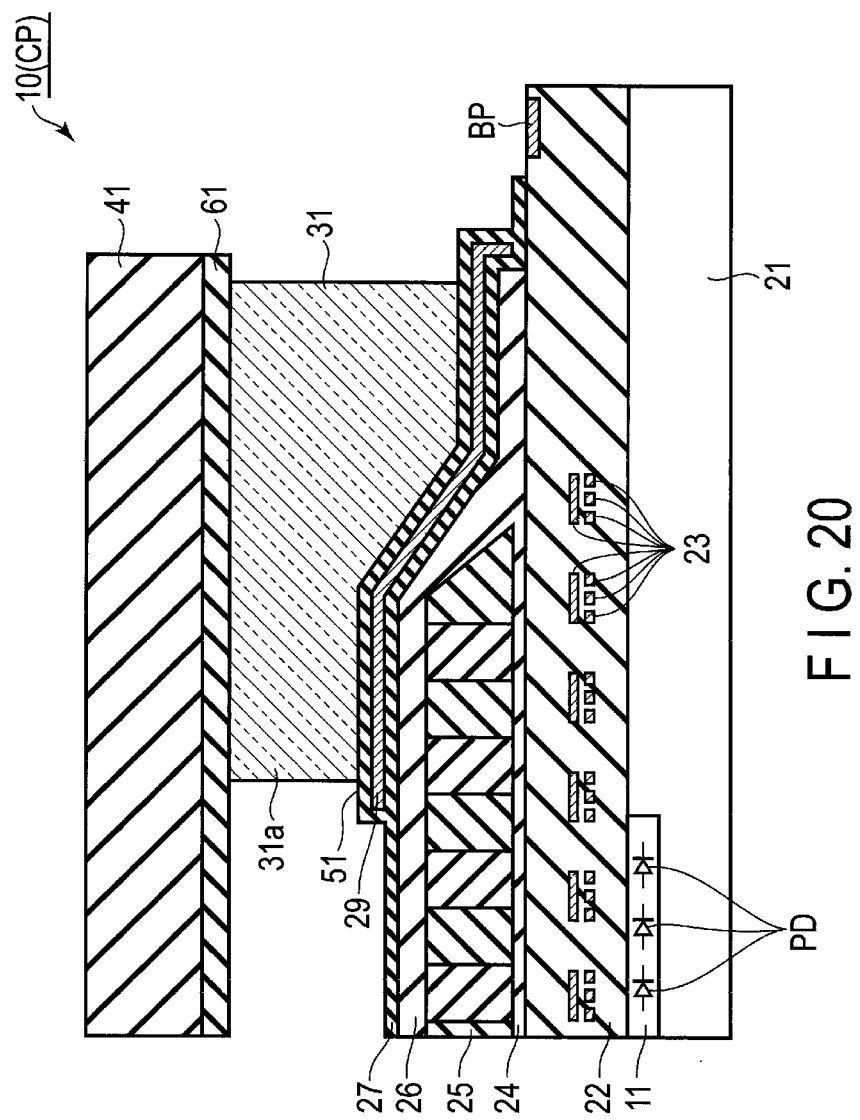
FIG. 20 is a cross-sectional view taken along line XX-XX of FIG. 17.

As shown in FIGS. 18, 19, and 20, for example, a black light absorption filter 61 is provided on a surface of a light shielding substrate 41, and a thick film material 31 is formed on the light absorption filter 61.

The light absorption filter 61 is formed of a material that absorbs an excitation light EL, and light including a wavelength of a fluorescence generated from the cell in the specimen solution.

When the light absorption filter 61 is provided, the light shielding substrate 41 is not limited to a silicon substrate, and may be a substrate having a light-transmitting property, such as a glass.

For example, an oxide film may be formed on the surface of the light absorption filter 61, in order to improve adhesion between a PDMS as the thick film material 31, and the light absorption filter 61.

Although a case where the sixth embodiment is applied to the fifth embodiment has been described, the sixth embodiment is not limited thereto. The sixth embodiment can be applied also to the fourth embodiment.

Effect of Sixth Embodiment

According to the sixth embodiment, the light absorption filter 61 is provided on the surface of the light shielding substrate 41, and the light absorption filter 61 contacts with the thick film material 31 arranged in the periphery of a pixel region 11. Thus, the light absorption filter 61 can reliably absorb the excitation light EL entered from the lateral side of a chip CP, the stray light entered from a bonding pad BP side of the chip CP, and the stray light entered from the light shielding substrate 41 side. Accordingly, photodiodes PD of the pixel region 11 can detect only the fluorescence generated from a cell in high sensitivity.

Seventh Embodiment

Figure 21:
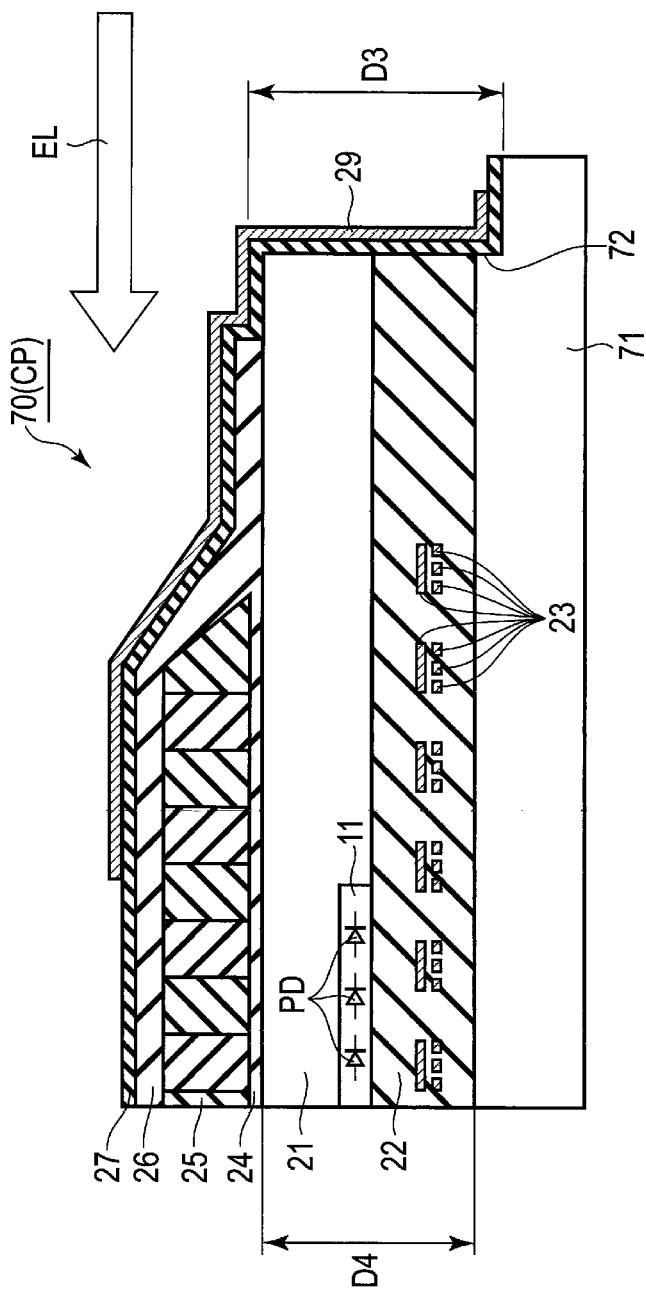
FIG. 21 is a cross-sectional view schematically showing an optical sensor according to a seventh embodiment.

FIG. 21 shows an optical sensor 70 according to a seventh embodiment. As the first embodiment to the sixth embodiment, the optical sensor 10 that is a front surface irradiation type has been described.

On the other hand, as the seventh embodiment, a case where the first embodiment is applied to an optical sensor 70 that is a rear surface irradiation type will be described.

As shown in FIG. 21, the configurations of a substrate 21 including a pixel region 11, and an insulation layer 22 including a plurality of wirings 23, are similar to those of the first embodiment to the sixth embodiment.

An upper surface of the insulating film 22 provided on the substrate (first substrate) 21 is bonded to a support substrate (second substrate) 71. That is, the insulating film 22 and the substrate 21 is stacked on the surface of the support substrate 71, in this order.

An insulating film 24 is provided on the rear surface of the substrate 21, and, for example, a color filter layer 25 is provided on the insulating film 24. An insulating film 26 as a protective film is provided on the color filter layer 25 and the insulating film 24.

A stepped portion 72 is formed in the support substrate 71 from the rear surface side of the substrate 21 through the insulation layer 22, and the substrate 21, the insulating film 22, and a side surface of the support substrate 71 are exposed. For example, in a state of wafer, the stepped portion 72 is formed by, for example, reactive ion etching (RIE) or half cutting such as dicing. A depth D3 of the stepped portion 72 is deeper than a depth D4 that is the sum of the thickness of the substrate 21 and the insulation layer 22.

A light-transmitting insulating film, for example, an inorganic insulating film 27 is provided in a rear surface of the substrate 21 including the insulating film 26, and a side surface and a bottom surface of the stepped portion 72.

A light-shielding film 29 is provided on the insulating film 27 excluding the pixel region 11, and at least in the side surface of the stepped portion 72.

Effect of Seventh Embodiment

According to the seventh embodiment, in the optical sensor 70 of the rear surface irradiation type, the light-shielding film 29 is provided on the insulating film 27 excluding the pixel region 11, and the side surface of the stepped portion 72, and irradiation with the excitation light EL is performed from the side surface side in which the stepped portion 72 of a chip CP is provided, substantially in parallel to the pixel region 11. Thus, irradiation of the excitation light EL performed from the lateral side of the chip CP can be prevented from entering the chip CP, and the pixel region 11 can detect the fluorescence generated from the cell in high sensitivity.

The light-shielding film 29 is formed in the side surface of the stepped portion 72, and the depth D3 of the stepped portion 72 is deeper than the depth D4 that is the thickness of the pixel region 11 in which the photodiodes PD are formed, and the insulating film 22 in which the plurality of wirings 23 are formed. Thus, since the light-shielding film 29 can shield the light advancing from the lateral side of the substrate 21 and the insulating film 22 toward the photodiodes PD, scattered light as the noise can be prevented from generating from the plurality of wirings 23 in the insulating film 22.

As the seventh embodiment, a case where the first embodiment is applied to the optical sensor of the rear surface irradiation type has been described. However, the seventh embodiment is not limited thereto. The second embodiment to the sixth embodiment can be incorporated to the optical sensor of the rear surface irradiation type according to the seventh embodiment, and the similar effect to those of the second embodiment to the sixth embodiment can be provided in the optical sensor of the rear surface irradiation type.

Eighth Embodiment

FIGS. 22 and 23 show an optical sensor 10 according to an eighth embodiment. As the first embodiment to the seventh embodiment, the optical sensor with a single chip in which one pixel region 11 is provided in one chip CP has been described.

On the other hand, as the eighth embodiment, an optical sensor with multiple chips in which a plurality of pixel regions 11 are provided in one chip will be described. Specifically, the optical sensor with multiple chips is formed by dicing processing a plurality of chips into one, from a state of a wafer.

FIGS. 22 and 23 show a case where the optical sensor 10 includes two chips, that is, a first chip CP1 and a second chip CP2. However, the optical sensor 10 is not limited thereto, and may include three or more chips. For example, three chips may be arranged in one column in a case of three chips, and four chips may be arranged in two rows and two columns in a case of four chips.

The configuration of the optical sensor shown in FIGS. 22 and 23 corresponds to the sixth embodiment. However, the configuration may correspond to the first embodiment to the fifth embodiment, or the seventh embodiment.

As shown in FIG. 23, the first chip CP1 and the second chip CP2 are arranged along an irradiation direction of an excitation light EL. For example, a stepped portion 28 is formed in a side surface of a substrate 21 including the first chip CP1, and, for example, a groove 30 is formed in the substrate 21 including the second chip CP2.

Specifically, for example, the grooves 30 are formed in the substrate 21 including the first chip CP1, and the substrate 21 including the second chip CP2, respectively, for example, by etching, and a light-shielding film 29 is formed across from an upper surface of an insulating film 27 into the groove 30. After that, the stepped portion 28 formed with the light-shielding film 29 is formed in the side surface of the substrate 21 including the first chip CP1 by performing dicing processing.

The grooves 30 are provided in both the first chip CP1 and the second chip CP2. However, when the light-shielding film 29 provided in the groove 30 of the first chip CP1 can provide sufficient light shielding, the groove 30 in the second chip CP2 can be omitted.

As shown in FIGS. 22 and 23, irradiation with the excitation light EL is performed from the lateral side of the first chip CP1. The excitation light EL passes a thick film material 31-1 of the first chip CP1, the inside of an accommodation unit 31a-1 of the first chip CP1 is irradiated with the excitation light EL, the excitation light EL passes the thick film material 31-1 of the first chip CP1 and a thick film material 31-2 of the second chip CP2 that are positioned in a boundary between the first chip CP1 and the second chip CP2, and the inside of an accommodation unit 31a-2 of the second chip CP2 is irradiated with the excitation light EL. Thus, it is preferable that the thick film material 31-1 of the first chip CP1 and the thick film material 31-2 of the second chip CP2 that are positioned in the boundary between the first chip CP1 and the second chip CP2, are integrally formed.

In a case where three chips are arranged in one column, when the three chips are arranged by the similar configuration to those in FIGS. 22 and 23, fluorescence from a cell can be simultaneously detected by one excitation light EL, with three chips.

When four chips are arranged in two rows and two columns, two chips shown in FIGS. 22 and 23 may be arranged in two columns and irradiation with the excitation light may be performed to each of the chips in the columns. In this case, the fluorescence from the cell can be simultaneously detected from the four chips.

Effect of Eighth Embodiment

According to the eighth embodiment, one optical sensor includes the first chip CP1 and the second chip CP2, the first chip CP1 includes a pixel region 11-1, and the second chip CP2 includes a pixel region 11-2. The thick film material 31-1 of the first chip CP1 and the thick film material 31-2 of the second chip CP2 are light transmitting materials. Thus, the fluorescence generated from the cell included in a specimen solution accommodated in the accommodation unit 31a-1 of the first chip CP1 and the accommodation unit 31a-2 of the second chip CP2, can be detected by one excitation light EL with which irradiation is performed from the lateral side of the first chip CP1. Accordingly, by using a plurality of chips, the fluorescence from the cell can be simultaneously detected by each of the chips. Thus, the detection efficiency can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An optical sensor comprising:
   a first substrate having a light detecting region detecting fluorescence generated from a fluorescent material by light with which irradiation is performed from a lateral side;
   a first insulating film provided on the first substrate; and
   a light-shielding film provided, at least, on a side surface of the first substrate to which the light enters, on a side surface of the first insulating film and above a region excluding a region corresponding to the light detecting region of the first insulating film.

2. The sensor of claim 1, further comprising
   a color filter provided above the first insulating film, wherein
   the light-shielding film shields the light entering a side surface of the color filter.

3. The sensor of claim 1, wherein
   the light detecting region includes a photoelectric conversion element, the first substrate comprises a recess in which the light-shielding film is provided, and the recess is deeper than a position of a layer in which the photoelectric conversion element is formed.

4. The sensor of claim 1, wherein
   the light-shielding film is one of a metal material and an insulation material, and when the light-shielding film is made of the metal material, a second insulating film is provided between the first substrate and the light-shielding film.

5. The sensor of claim 1, further comprising
   a light transmitting film provided on the light-shielding film in a periphery of the light detecting region, and transmitting the light.

6. The sensor of claim 5, further comprising
   a second substrate provided on the light transmitting film, covering the light detecting region, and having a light shielding property.

7. The sensor of claim 6, further comprising
   a third insulating film provided between the light-shielding film and the light transmitting film.

8. The sensor of claim 7, wherein
   the second substrate comprises a filter absorbing the light from the second substrate.

9. The sensor of claim 8, wherein
   the first insulating film includes a bonding pad, and the bonding pad is exposed from the second substrate.

10. An optical sensor comprising:
    a first substrate having a first surface and a second surface parallel to the first surface, and having a light detecting region detecting fluorescence generated from a fluorescent material by light irradiated from a lateral side;
    a first insulating film provided on the second surface of the first substrate;
    a second substrate supporting the first insulating film; and
    a light-shielding film provided on a side surface of the first substrate, on a side surface of the first insulating film, on a side surface of the second substrate and on a region excluding a region corresponding to the light detecting region in the first surface of the first substrate, and shielding the light.

11. The sensor of claim 10, further comprising
    a color filter provided above the first surface of the first substrate, wherein
    the light-shielding film shields the light entering a side surface of the color filter.

12. The sensor of claim 10, wherein
    the light detecting region includes a photoelectric conversion element, the first substrate and the first insulating film comprises a recess arranged in a crossing direction with an incident direction of the light and the light-shielding film is provided therein, and the recess is deeper than a position of a layer in which the photoelectric conversion element is formed.

13. The sensor of claim 10, wherein
    the light-shielding film is one of a metal material and an insulation material, and when the light-shielding film is made of the metal material, a second insulating film is provided between the first substrate and the light-shielding film.

14. The sensor of claim 10, further comprising
    a light transmitting film provided on the light-shielding film in a periphery of the light detecting region, and transmits the light.

15. The sensor of claim 14, further comprising
    a third substrate provided on the light transmitting film, covering the light detecting region, and having a light shielding property.

16. An optical sensor comprising:
    a first substrate having a first light detecting region and a second light detecting region which are arranged along an irradiation direction of light and detect fluorescence excited by the light from a fluorescent material;
    a first insulating film provided on the first detecting region;
    a second insulating film provided on the second light detecting region; and
    a light-shielding film provided, at least, on a side surface of the first substrate to which the light enters, on a side surface of the first insulating film and above a region excluding regions corresponding to the first light detecting region of the first insulating film, and shielding the light.

17. The sensor of claim 16, further comprising:
    a first color filter provided above the first insulating film; and
    a second color filter provided above the second insulating film, wherein
    the light-shielding film shields the light entering a side surface of the first color filter.

18. The sensor of claim 16, wherein
    the first light detecting region includes a first photoelectric conversion element, the first substrate and the first insulating film are provided in a crossing direction with an incident direction of the light, and have a recess provided the light-shielding film therein, and the recess is deeper than a position of a layer in which the photoelectric conversion element is formed.

19. The sensor of claim 16, wherein
    the light-shielding film is one of a metal material and an insulation material, and when the light-shielding film is made of the metal material, a third insulating film is provided between the first substrate and the light-shielding film.

20. The sensor of claim 16, further comprising
    a light transmitting film provided on the light-shielding film in a periphery of the first light detecting region, and transmits the light.

* * * * *